US 9,445,764 B2

(12) United States Patent
Gross et al.

(10) Patent No.: US 9,445,764 B2
(45) Date of Patent: Sep. 20, 2016

(54) METHOD FOR AUTOMATIC SETTING TIME VARYING PARAMETER ALERT AND ALARM LIMITS

(75) Inventors: Brian D. Gross, North Andover, MA (US); Jyh-Yun J. Wang, Newton, MA (US); Marcus Holland-Moritz, Gartringen (DE); Bernd Wilm, Rohrdorf (DE); Axel Lange, Stuttgart (DE); Benedikt Latz, Stuttgart (DE); Volker Manfred Hubert, Gaertringen (DE); Gerhard Tivig, Nufringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 714 days.

(21) Appl. No.: 13/383,736

(22) PCT Filed: Jun. 15, 2010

(86) PCT No.: PCT/IB2010/052681
§ 371 (c)(1),
(2), (4) Date: Jan. 12, 2012

(87) PCT Pub. No.: WO2011/007271
PCT Pub. Date: Jan. 20, 2011

(65) Prior Publication Data
US 2012/0116194 A1     May 10, 2012

Related U.S. Application Data

(60) Provisional application No. 61/225,702, filed on Jul. 15, 2009.

(51) Int. Cl.
*A61B 5/00* (2006.01)
*G06F 19/00* (2011.01)
(Continued)

(52) U.S. Cl.
CPC ............... *A61B 5/4839* (2013.01); *A61B 5/00* (2013.01); *A61B 5/0452* (2013.01); *G06F 19/345* (2013.01); *G06Q 50/22* (2013.01);
(Continued)

(58) Field of Classification Search
CPC  A61B 5/0006; A61B 5/0024; A61B 5/0205; A61B 5/02455; G06F 19/34; G06F 19/3406; G06F 19/3418
USPC ......... 600/300, 301; 128/903–905, 920–925, 128/898
See application file for complete search history.

(56) References Cited

U.S. PATENT DOCUMENTS

| 5,464,012 A | 11/1995 | Falcone |
| 7,079,035 B2 * | 7/2006 | Bock et al. ............... 340/573.1 |
| 2002/0169366 A1 | 11/2002 | Schmidt et al. |

(Continued)

FOREIGN PATENT DOCUMENTS

| WO | 0010455 A1 | 3/2000 |
| WO | 0232304 A1 | 4/2002 |
| WO | 03098385 A2 | 11/2003 |

*Primary Examiner* — William Thomson
*Assistant Examiner* — Nathan J Jenness

(57) ABSTRACT

When monitoring physiological parameters (e.g., blood pressure, heart rate, etc.) of a patient, a threshold limit (30) is set (e.g., automatically or manually) and the monitored parameter is continuously compared to the threshold limit, which may be constant or may vary with time. An alarm (36) is triggered if the monitored parameter exceeds the threshold limit at any time, or if the monitored parameter has not reached a target value by the end of a predefined time period by which an administered drug or therapy should have been effective.

22 Claims, 6 Drawing Sheets

(51) Int. Cl.
*A61B 5/0452* (2006.01)
*G06Q 50/22* (2012.01)
*A61B 5/021* (2006.01)
*A61B 5/024* (2006.01)
*A61B 5/1455* (2006.01)

(52) U.S. Cl.
CPC ............... *A61B 5/021* (2013.01); *A61B 5/024* (2013.01); *A61B 5/1455* (2013.01); *A61B 2560/0276* (2013.01); *G06F 19/3487* (2013.01)

(56) References Cited

U.S. PATENT DOCUMENTS

| | | | |
|---|---|---|---|
| 2003/0018241 A1* | 1/2003 | Mannheimer | 600/300 |
| 2005/0228234 A1 | 10/2005 | Yang | |
| 2007/0016115 A1 | 1/2007 | Buchholtz et al. | |
| 2007/0232867 A1* | 10/2007 | Hansmann | 600/300 |
| 2008/0061961 A1 | 3/2008 | John | |
| 2008/0086035 A1* | 4/2008 | Messerges et al. | 600/300 |
| 2009/0043182 A1* | 2/2009 | Brauker et al. | 600/347 |

* cited by examiner

METHOD FOR AUTOMATIC SETTING TIME VARYING PARAMETER ALERT AND ALARM LIMITS

CROSS REFERENCE TO RELATED APPLICATIONS

This application claims the benefit of U.S. provisional application Ser. No. 61/225,702 filed Jul. 15, 2009, which is incorporated herein by reference.

The present innovation finds application in patient monitoring systems, particularly with regard to physiologic monitoring systems. However, it will be appreciated that the described techniques may also find application in other monitoring systems, other healthcare information collection scenarios, other status monitoring techniques, and the like.

Current physiologic monitoring of the patient require that each parameter have the capability to announce an alarm should the parameter exceed set limits. Nominally these limits are user set and create alerts for each time the patient's physiology changes past the set limit. When therapies are initiated such as coronary artery angioplasty or initiation of a vasoactive drug, the parameter limits are typically not changed by the care giver. In some cases the desired effect of an intervention is accommodated by the user's manual change for the target physiology; however there are unexpected effects on other parameters, which the user does not consider when they establish new alert levels for the initiated intervention. Further, the clinician typically is interested in being notified that the clinical parameters have not responded appropriately to the intervention or therapy ongoing or even wanted to be notified if the intervention was successful. Further, the clinician is interested in knowing the indicated changes to the current workflow based on the current patient response to therapy including the need for new clinical data such as blood laboratory results, or subjective responses to therapy.

Many treatments do not provide instantaneous improvement. Rather, physiologic signals including vital signs frequently continue to deteriorate until the treatment takes effect. If the limits are held unchanged, false alarms result. If the limits are not optimized to the physiologic expectations of the intervention, meaningful feedback regarding whether the patient has started to improve as expected is lost.

These "worsening" or "not improving" criteria are sometimes implemented as a written order to manually check the parameter in question after a given time span and contact the ordering physician if the parameter is not in the target range. In other cases the lack of improvement or worsening conditions are discovered late or not at all, resulting in a delay of the correct treatment. During this time alarms triggered by the monitoring system because the intervention is not yet effective are often ignored, perceived as false or meaningless, or the alarms are switched off.

In physiologic monitoring systems that trigger an alarm or an alert in response to one of the measured physiological parameters exceeding a threshold, the threshold is set, typically by a clinician, and remains stationary. After a medical intervention or therapy, the patient is expected to improve, typically with a lag time. The time lag will depend on the patient's starting state, the physiologic response to the intervention and many other variables. It is also important for the clinician to know whether the patient is, in fact, improving. Typically, monitoring for improvement in response to the intervention or therapy is done manually, and lack of timely improvement is easily overlooked.

The present application provides new and improved systems and methods for alerting a clinician to a patient need based on a comparison of monitored parameter value to a threshold or limit value as a function of time, which overcome the above-referenced problems and others.

In accordance with one aspect, a method of providing a time-varying physiological parameter alert comprises monitoring a physiologic parameter, patient data, or clinical information of a patient, and comparing the monitored parameter to an initial threshold criteria. Following a drug administration, intervention or therapy administration event, the initial threshold criteria is temporarily changed to a worsened condition threshold criteria that permits worsening of the monitored parameter for an allotted time period and to a post-administration threshold criteria after the allotted time period. During the allotted time period, the monitored parameter is compared to the worsened condition threshold criteria, and after the allotted time period, the monitored parameter is compared to the post-administration threshold criteria. The method further includes triggering an alarm in response to the monitored parameter violating one or more of the initial threshold criteria, the worsened condition threshold criteria, and the post-administration threshold criteria.

In accordance with another aspect, a system that provides a time-varying physiological parameter alert to a user comprises one or more sensors that monitor a physiological parameter of a patient, and a processor programmed to receive one or more of patient data, clinical lab data, and monitored data or measurements that describe the physiological parameter. The processor is further programmed to compare the monitored parameter to an initial threshold criteria. Following a drug administration, intervention or therapy administration event, the processor temporarily changes the initial threshold criteria to a worsened condition threshold criteria that permits worsening of the monitored parameter for an allotted time period and to a post-administration threshold criteria after the allotted time period. During the allotted time period, the processor compares the monitored parameter to the worsened condition threshold criteria. After the allotted time period, the processor compares the monitored parameter to the post-administration threshold criteria. In response to the monitored parameter violating one or more of the initial threshold criteria, the worsened condition threshold criteria, and the post-administration threshold criteria, the processor triggers an alarm.

In accordance with another aspect, a system that provides for triggering of workflow or the need for additional clinical information based on the response to a defined drug administration, therapy, or intervention event.

One advantage is that time spent interpreting the response of an initiated therapy for a patient is reduced.

Another advantage is that the detection of a patient's non-response to an intervention is detected quicker.

Another advantage is that the threshold limit changes with treatment expectations.

Another advantage is that the number of action-less alerts or alarms is minimized.

Still further advantages of the subject innovation will be appreciated by those of ordinary skill in the art upon reading and understanding the following detailed description.

The drawings are only for purposes of illustrating various aspects and are not to be construed as limiting.

Figure 1:
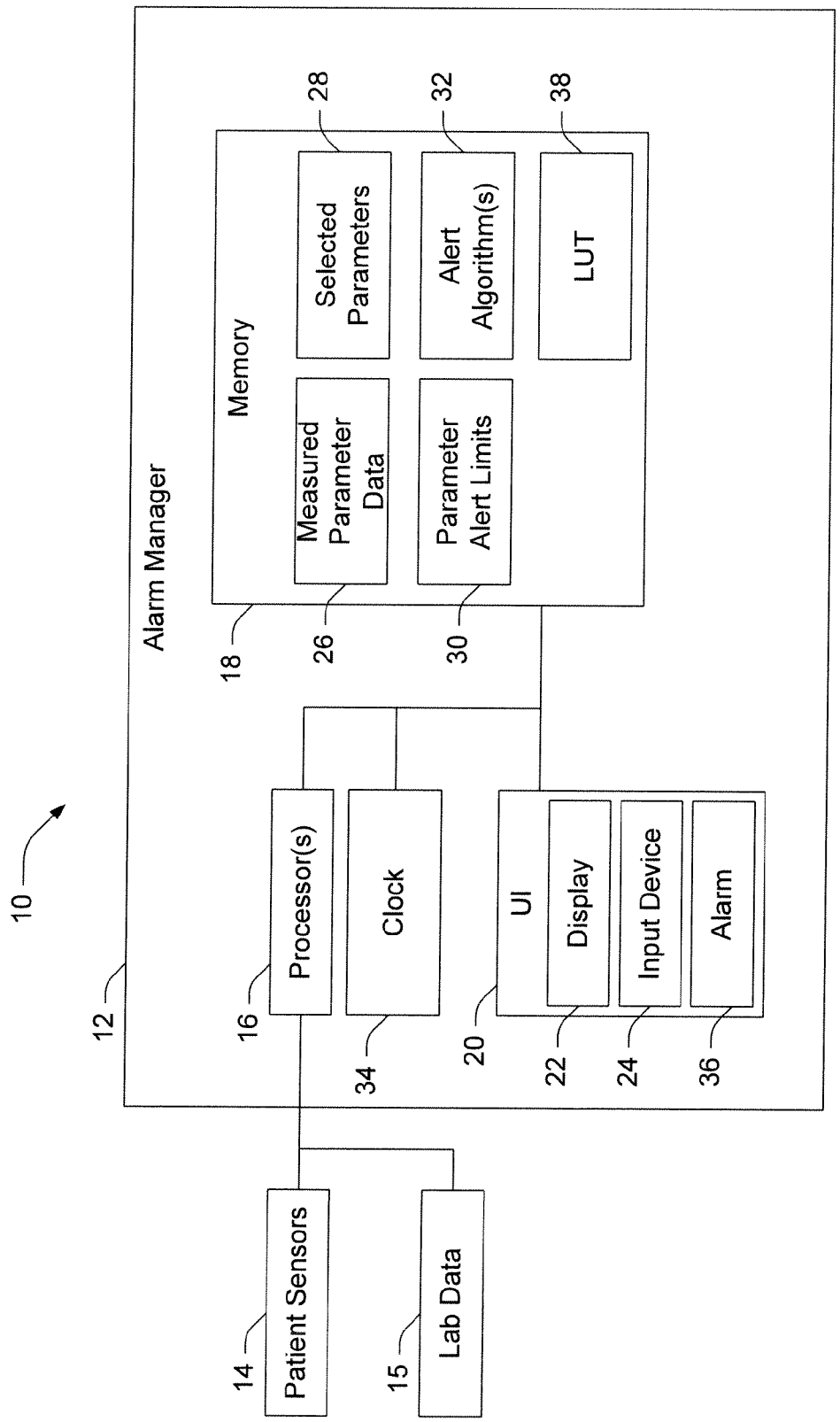
FIG. 1 illustrates a system that facilitates providing a time-varying alert behavior that may be automatically adjusted by the system, or manually programmed by a user, to adjust an alert setting that triggers an alert message and notification of a patient's need.

FIG. 1 illustrates a system 10 that facilitates providing a time-varying alert behavior that may be automatically adjusted by the system, or manually programmed by a user, to adjust an alert setting that triggers an alert message and notification of a patient's need. For instance, the system monitors a patient and triggers an alarm if or when the patient's condition does not improve within a predetermined time period or window.

The system 10 includes an alarm manager 12 coupled to one or more patient sensors 14, clinical data 15, which may include historical physiological information, knowledge rules, etc. The sensors 14 are couple to a patient to sense or measure patient parameters (e.g., temperature, heart rate, respiration rate, blood pressure, blood-oxygen level (SpO2), blood sugar level, blood-metabolite level for a desired metabolite, ECG waveform, or any other measurable or subjective parameter of wellness). The monitor includes a processor 16 executes, and a memory 18 that stores, computer executable instructions for performing the various techniques, methods, actions, etc., described herein. The processor and memory are coupled to a user interface 20 that includes a display 22 for presenting information (e.g., patient parameter information, alerts, etc.) to a user, and an input device 24 by which a user enters information to the monitor. The input device may be a mouse, a stylus, a keyboard, a touch screen, a voice activated input device, or any other suitable device for entering information into the user interface of the monitor.

The processor 16 receives measured parameter data 26 from the patient sensor(s) 14 and/or clinical data 15, stores it in the memory 18, and displays it on the display 22. Additionally, the processor can receive data indicative of interventions, drug and/or therapy administration, etc., from external systems and/or from a user. The system selects one or more parameters and selected parameters 28 are stored in the memory 18. The user then sets one or more parameter alert limits 30 (e.g., ranges or thresholds such as a time range, a parameter magnitude range, "improvement" time function, parameter threshold value, etc.), which are stored in the memory 16. Upon activation by the user or availability of required data to execute, the processor continuously executes an alert algorithm (e.g., a set of computer-executable instructions) that monitors the selected parameter(s) 28 to determine whether an indicated range or threshold limit has been surpassed. If the parameter alert limits include a time range, a clock 34 (e.g., a timer, a real-time clock, a counter, or the like) in the monitor provides time information to the processor and/or the alert algorithm(s) for use in determining whether a predefined or selected time or time range has expired. Upon detecting that a selected parameter has exceeded a limit or has passed out of an indicated range, the processor triggers an alarm 36 in the user interface to alert a clinician that the patient or workflow needs attention.

According to an example, upon administering an intervention (e.g., a drug) or therapy, a selected patient parameter may deteriorate for some period of time. Then, when the intervention or therapy becomes active (e.g., is metabolized by the patient, reaches a target organ or site, etc.), improvement of the selected parameter is expected. Either through an automatic interface (not shown) or via the user using the input device 24, information describing which intervention or therapy was initiated is indicated. The system determines if any parameters 28 available are subject to alarm or alert modification. If so the parameter limits are adjusted by the system thus permitting limited deterioration for the selected parameter for a limited latent time period following the intervention (mitigate false or premature alarms). Then, after a user-configured time period for the intervention or therapy to become effective, the limit is automatically adjusted (e.g., lowered or raised, depending on the parameter and/or the expected effect of the drug or treatment) to a level that reflects improvement of the selected parameter. In one embodiment, the changes in the limits are initially raised, and then reduced upon expiration of a time period after which the intervention is expected to be effective. In another embodiment, after the latent period for the intervention or therapy to become effective, the limit is adjusted to follow a smooth curve that changes over time. In another embodiment, the limit is adjusted in a series of small steps, over time. In all of these embodiments, if the patient's condition is not improving as expected after the intervention or therapy, the processor 16 signals the alarm 36 to notify the clinician that the intervention or therapy is not producing the desired effect, or the condition is worsening in spite of the intervention.

The adjustment of the parameter limit(s) with time can be done in various ways. In one embodiment, the monitor determines the time-changing threshold limit automatically by inference from the monitored physiological parameters, their historical value, and/or by interfacing with other systems or databases (not shown). For example, if the device is also monitoring an IV pump with a given medication, then the monitor can receive information related to the medication and the pumping rate and can infer an expected improvement. The memory therefore includes a knowledge data base or look-up table 38 or the like with curves for various conditions and interventions or treatments based on what is known about the patient, the historical physiology and the intervention initiated. Optionally, the lookup table can be stored remotely from the monitor, such as in a network database (not shown) or the like.

In another embodiment, the processor 16 displays the proposed limit curve on the display 22, and the operator is able to adjust the curve. In another embodiment, the changes in limit versus time are set manually using the input device 24.

According to another embodiment, multiple physiological parameters can be monitored. These parameters may be related directly to the physiological condition of the patient or to the effects for which the intervention or therapy was performed. Alternately, the change in parameter threshold or limit can also be based on physiological parameters indicative of known side effects of the intervention or treatment. For example, medications administered to raise blood pressure typically also raise heart rate. Thus, where a patient's heart rate is maintained above a limit setting during a selected time range after administration of such a medication, but blood pressure dips below a minimum blood pressure limit setting, or the heart rate increases above the new temporary permitted level preconditioned on the intervention, the processor 16 can trigger the alarm 36 to alert a clinician to the event.

The parameter alert limits 30 can be in the form of a simple threshold (e.g., "High HR" alarm if HR>High HR Limit), or can be severity-based where different alerts are issued for the same parameter based on a medium priority alert limit, a high priority alert limit, a sophisticated algorithm that detects a physiological alarm event, etc. Additionally, the monitor 12 can display an automatic or manually-input indication that a therapy or intervention was initiated, or a parameter has violated its current parameter limits. For example, via device interfacing, or user activation, system knowledge of the administration of medications or interventions, or knowledge that a current parameter value exceeds a current parameter limit can be displayed on the display 22.

The system 10 also enables automatic or manual setting of a "worsening condition" alarm setting that temporarily loosens or allows a wider variation of the parameter for the a current alarm limit. This temporary condition is allowed as long as therapeutic intervention is not yet effective, but if the parameter violates this new temporary limit, the user can be notified of a worsening condition. For instance, if a patient is given a beta-blocker to reduce heart rate and/or blood pressure, and the medication typically takes approximately 30 minutes to become effective in the patient, then the user sets the worsening condition alarm setting to block a current alarm condition (e.g., high blood pressure and/or heart rate) for 30 minutes. The system can allow the patient's heart rate to continue to increase to a "worsening limit", but at the expiration of 30 minutes, if the patient's heart rate and/or blood pressure are still above the expected improvement limit, then the alarm will sound to alert the user to the "not improving" condition. In this manner, a clinician need not continually check back in on the patient while still being alerted to these conditions, or can be notified more promptly.

The system 10 permits automatic or manual setting of the desired parameter alert limits 30 to the expected response curve and the time function that a selected parameter is expected to follow. Additionally, the system permits automatic or manual setting of hazardous conditions associated with the intervention or administration, as well as the time function the selected parameters are expected to follow. These features are provided as a function of parameters available to the system, a physiological model of the patient based on historical knowledge of parameter behaviors, clinical guidelines, etc.

In this manner, physiologic data collection is facilitates with an alarm management functionality capable of comparing the current parameter measurement values 26 to configured parameter alert limits 30. In addition, the system 10 has access to intervention and therapy information about the patient including medication administration, dose, and therapeutic category. Finally the system facilitates calculating calculate a therapeutic target as a function of time, as well as conditioning worsening criteria.

With regard to the processor 16 and the memory 18, it will be understood that the processor 16 executes, and the memory 18 stores, computer-executable instructions for carrying out the various functions and/or methods described herein. The memory 18 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 16 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

Figure 2:
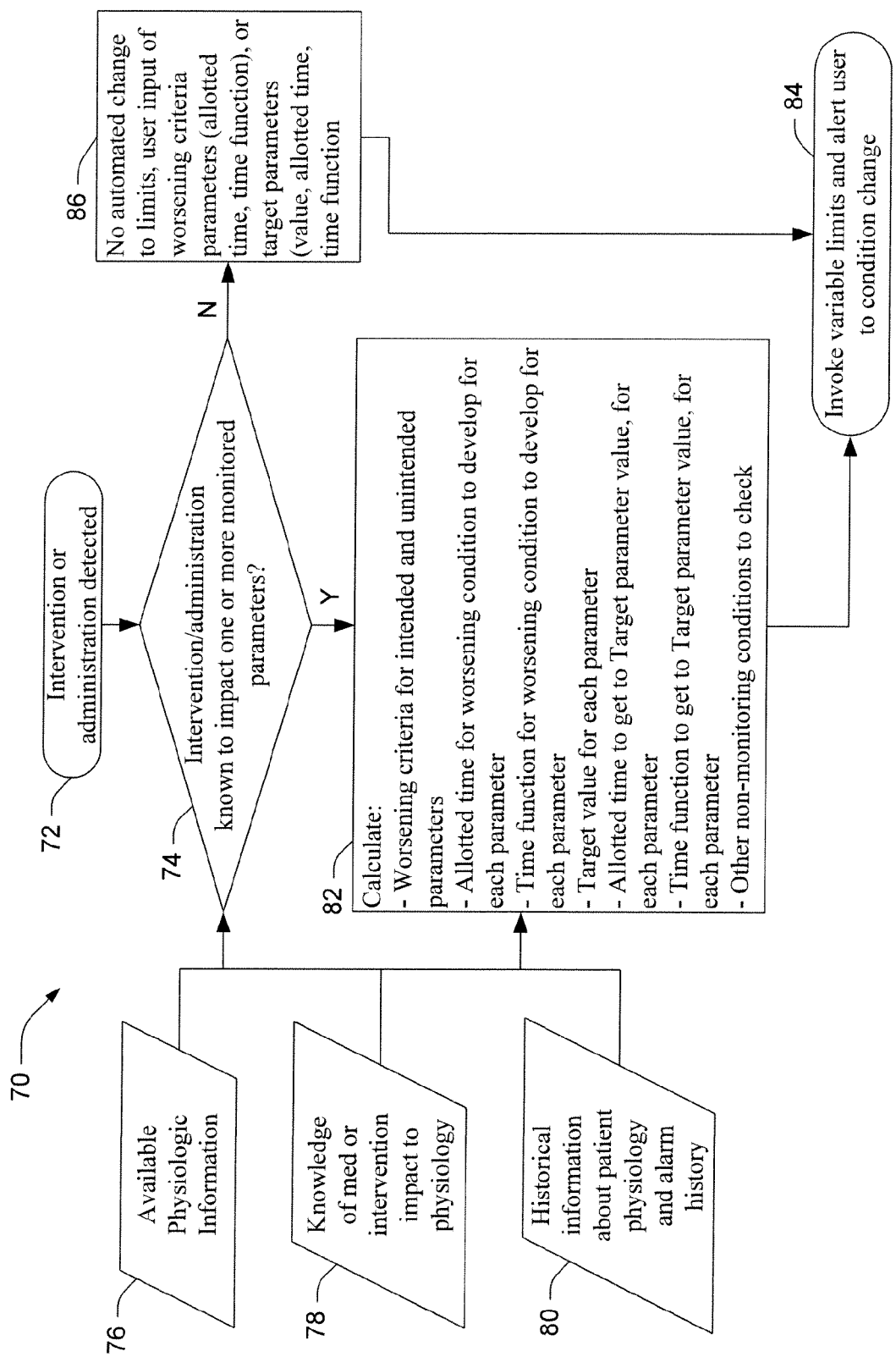
FIG. 2 illustrates a process flow for collecting and displaying physiologic data with an alarm management system that compares current physiologic parameter values to configured alarm limits.

With continued reference to FIG. 2, a process flow 70 collects and displays physiologic data with an alarm management system that compares current physiologic parameter values to configured alarm limits. At 72, an intervention or administration (e.g., therapy, drug, etc.) is detected or input. At 74, a determination is made regarding whether the detected event is known to impact one or more monitored parameters. For instance, if the administration event is an administration of a vasoactive drug that increases blood pressure, and patient blood pressure is being monitored, then the determination will be affirmative.

Multiple data sources are employed in making the determination at 74. For instance, available physiologic information 76 (e.g., monitored parameters or the like) may be contemplated, as well as knowledge 78 of medical or intervention impact to physiology (e.g., expected effects, measured effects, etc.). Additionally, historical information 80 describing patient physiology and alarm history may be employed in making the determination at 74. If the determination is affirmative, then at 82, several factors are calculated by the system 10 (FIG. 1).

For instance, at 82, a worsening, not improving, or indicated workflowcriteria for intended and/or unintended parameters is calculated. An allotted time period for a worsening condition to develop (e.g., for reaching a threshold limit) for each monitored or impacted parameter is calculated as well. The system 10 additionally calculates a time function for the worsening condition to develop for each monitored or impacted parameter, as well as a target value for each parameter. Moreover, an allotted time period to achieve the target parameter value for each monitored or impacted parameter is calculated by the system, as is a time function to achieve the target parameter value for each monitored or impacted parameter. Other non-monitored conditions to check are also identified at 82. At 84, variable limits are invoked and a user (e.g., a clinician, nurse, physician, or the like) is alerted to the condition change.

If the determination at 74 is negative, then at 86 no automated change is made to the limit values (although user adjustment is permitted), to the user input of worsening criteria parameters (e.g., allotted time, time function, etc.) or target parameters (e.g., values, allotted time, time function, etc.). The process flow then proceeds to 84, where variable limits are invoked and a user (e.g., a clinician, nurse, physician, or the like) is alerted if necessary.

With continued reference to FIGS. 1 and 2, and further reference to FIGS. 3-6, several graphical examples are illustrated in which a patient has received a percutaneous coronary intervention (PCI) intervention (e.g., an angioplasty procedure or the like), or wherein via device interfacing, system interfacing, or user activation, the system 10 (FIG. 1) gains knowledge of the administration of a medication where the therapeutic category of the drug and dose is classified as "thrombolytic", because of an acute ST segment (e.g., the portion of an electrocardiogram between the end of the QRS complex and the beginning of the T wave) elevated myocardial infarction.

Figure 3:
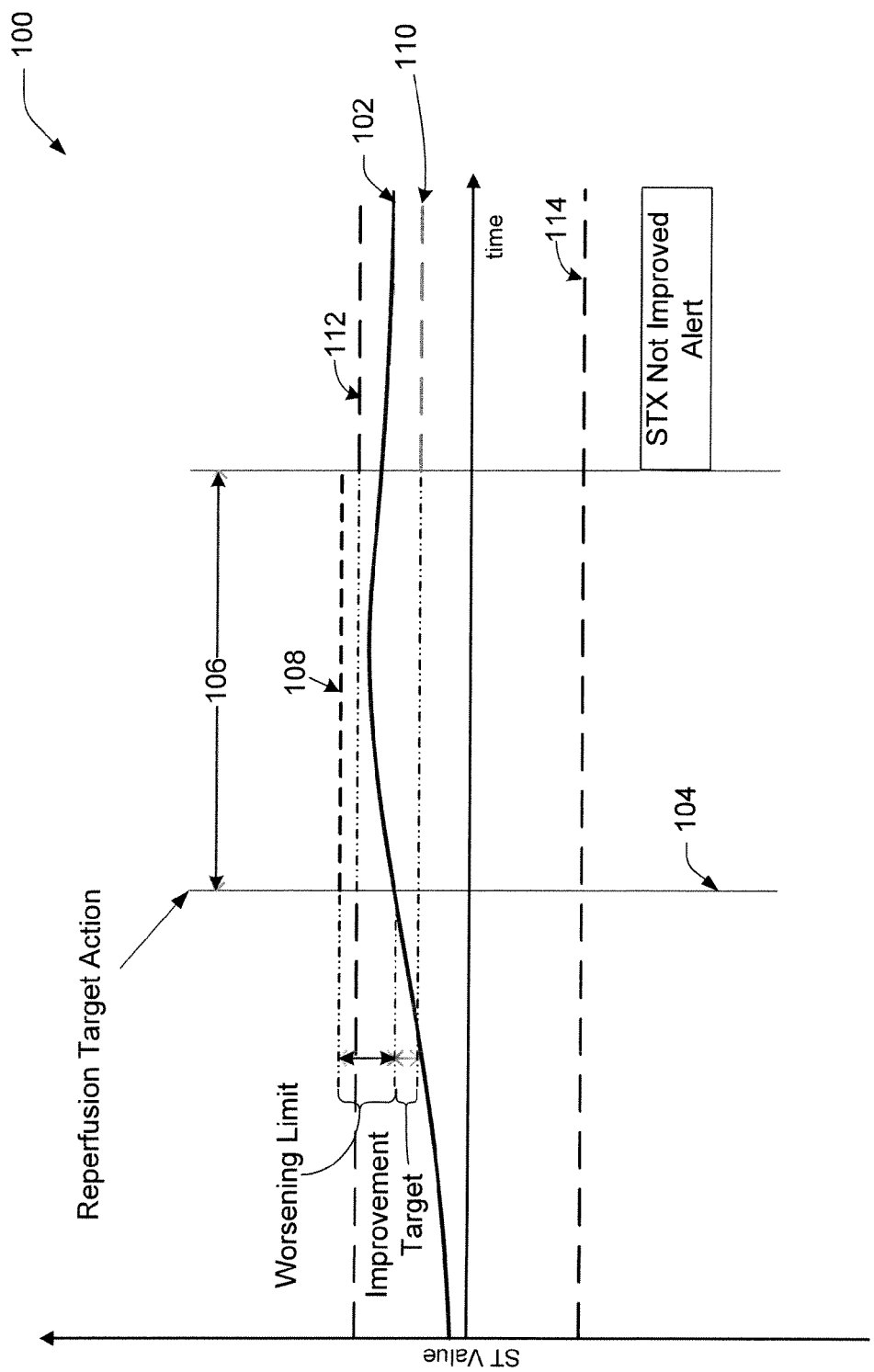
FIG. 3 illustrates a graph in which values of the ST segment of the ECG waveform are monitored (e.g., by the patient sensor(s), and the system has automatically, or the user has manually indicated to the system (or by automatic data interfaces), that the intervention was completed, and the recovery has initiated a "not improving" alarm.

FIG. 3 illustrates a graph 100 in which The ST values 102 are monitored (e.g., by the patient sensor(s) 14 such as ECG electrodes (FIG. 1), and the system has automatically, or the user has manually indicated to the system (or by automatic data interfaces), that the intervention was completed 104. Once the trigger has occurred, the system independently calculates worsening and improving criteria and time constants based on clinical guidelines such as, e.g., 1 mm is "worsening" and 50% improvement in 60 minutes is "improvement" or "reperfusion target". The upper ST "worsening" limit is a step change over time 108.

In FIG. 3, the monitored ST value is shown as a solid line 102. A reperfusion target action triggers the beginning 104 of an expected improvement time period 106. A (e.g., a threshold limit) temporarily worsening ST limit 108 which is calculated from pre-intervention alarm limit 112 and an improvement target 110, which may be user-determined or may be automatically set by the system, are also illustrated. An upper user ST limit 112, which is the same as the pre-intervention upper ST limit, is set after the expected improvement. A lower user ST limit 114 delineates an ST value below which a ST Low alarm will be triggered. In this case the worsening/not improving limit modification need only be applied to leads involved with the culprit vessel involved in the intervention and only the elevated ST leads (and not the depressed ST leads). Additionally, an "ST-X Not Improving" alert or alarm is triggered at the expiration of the expected improvement time period of the patient's ST value is not improved below to the upper target improvement limit 110. It should be noted that the terms of above and below limits are relevant to the clinical scenario described herein and are employed to represent the clinical condition and expected physiologic parameter trajectory.

Figure 4:
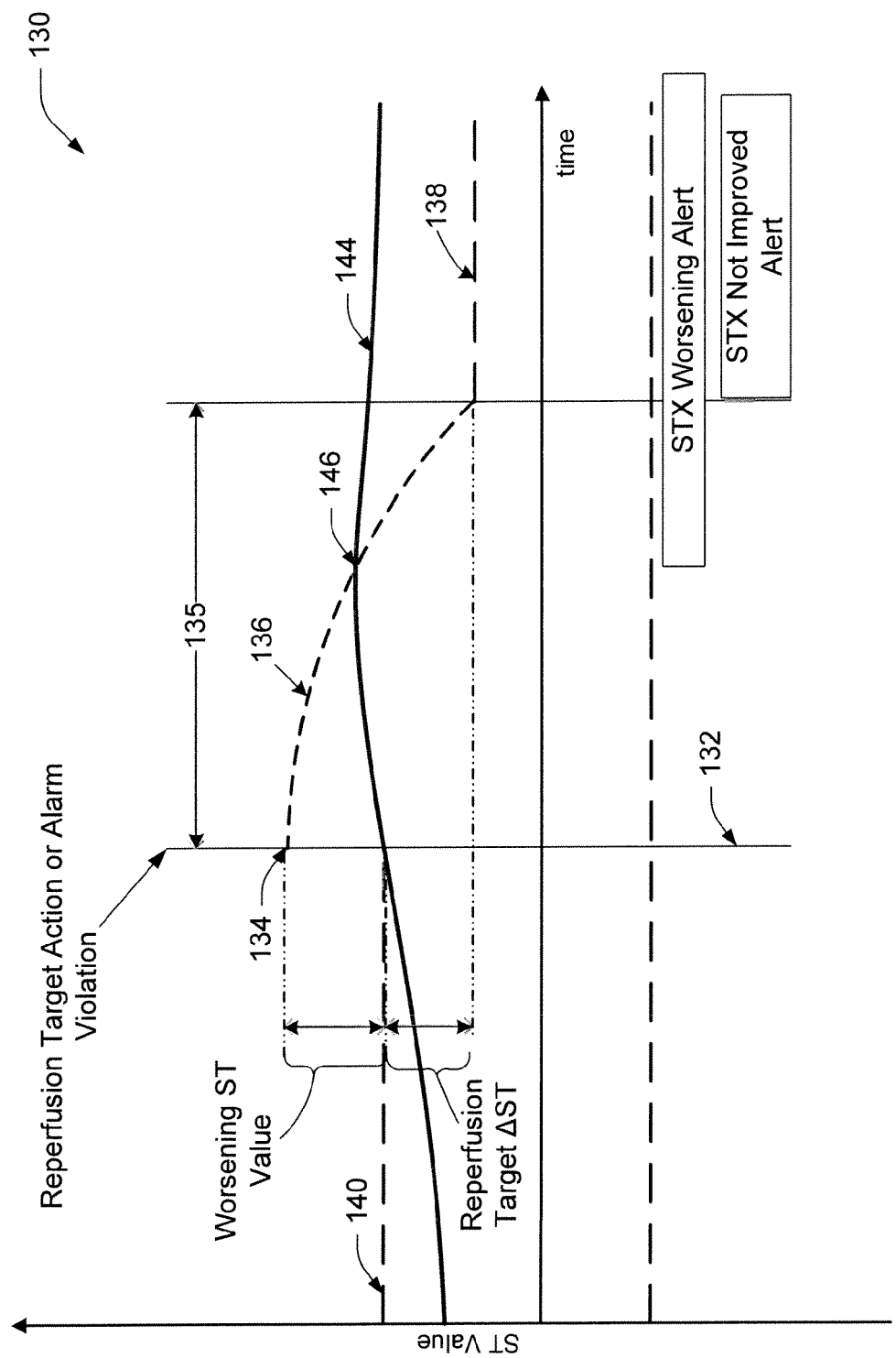
FIG. 4 illustrates a graph wherein the worsening ST limit is a monitonically decreasing function from the initial higher worsening ST limit value to an original or default high limit value (the reperfusion target limit), and the result is both a "worsening" and "not improving" alarm.

FIG. 4 illustrates a graph 130 wherein at a time 132 of performing the therapeutic action, the worsening upper ST limit is increased to an initial higher (relative to FIG. 3) worsening ST limit value 134. During an expected improvement time 135, the upper ST limit decreases along a smooth monotonically decreasing curve 136 to a new upper ST limit 138 which, in this example, is lower than the original upper ST limit 140. In this example, an "ST-X Worsening" alert is triggered by the alert subsystem 36 when the worsening upper ST limit 136 and the patient's monitored ST value 144 cross at 146. An "ST-X Not Improved" alert is also triggered at the expiration of the expected improvement time period 135.

Figure 5:
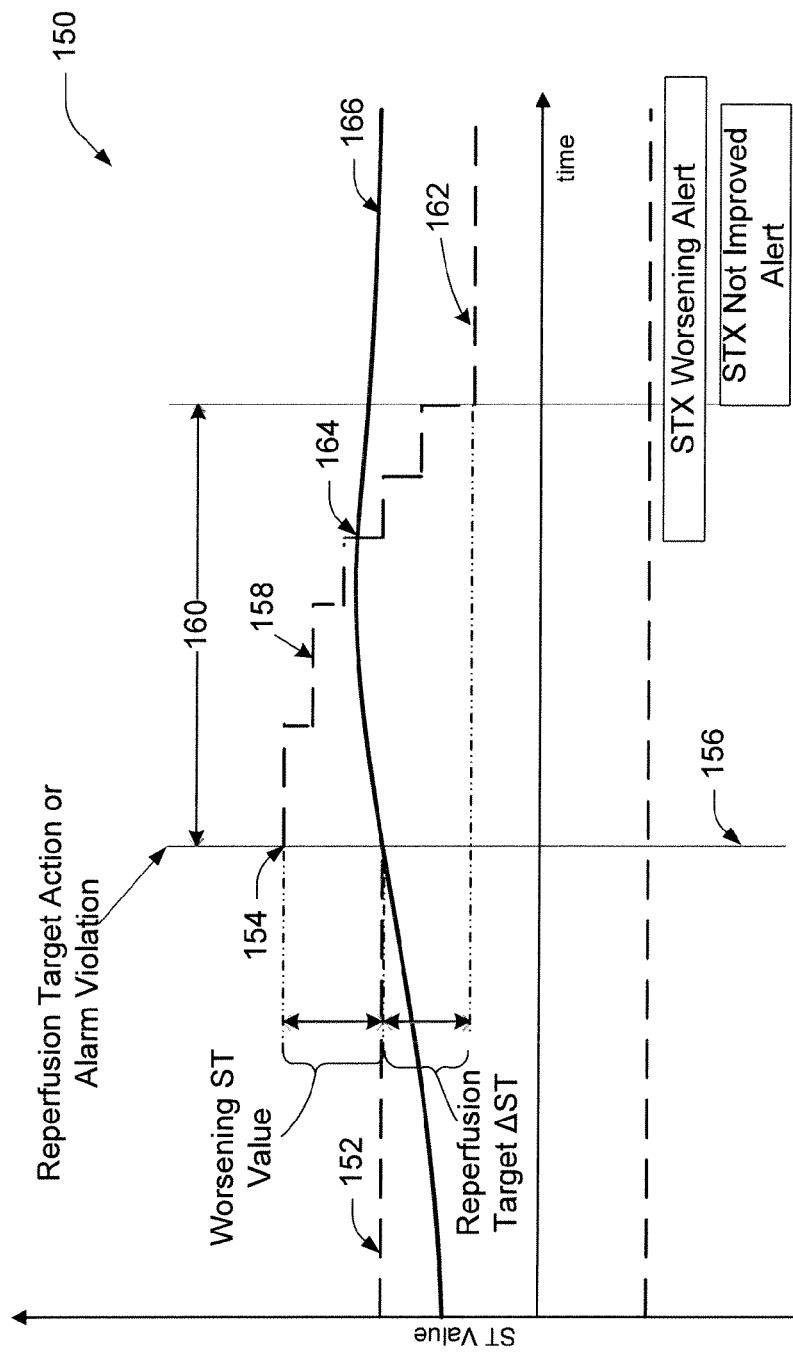
FIG. 5 illustrates a graph wherein the new high limit is reduced in a series of step levels over the time duration to the improvement threshold.

FIG. 5 illustrates a graph 150 wherein a high ST limit 152 is stepped to a new high limit 154 (relative to FIG. 3) at a time 156 of the therapeutic action. The high limit is reduced in a series of uniformly decreasing step levels 158 over an expected improvement time duration 160 to a new improvement threshold upper ST limit 162. An "ST-X worsening" alert is triggered at a time 164 when the upper ST limit 158 the patient's monitored ST value 166 cross. An "ST-X not improved" alert is triggered at the expiration of the expected improvement time period 160 when the monitored ST value 164 still exceeds the improvement threshold upper limit 162.

In each of these examples, a unique condition threshold, inhibitory period, and delay time is established. Each of the conditions can result in notification to the user of a worsening condition, a condition that is not improving per target time envelope, or that improvement was achieved in the desired time envelope using a variety of worsening time functions for which the worsening criteria is tested.

In one embodiment, a continuous infusion where the therapeutic category of the drug and dose is classified as "vasopressor" and blood pressure (BP) is monitored. The system calculates the delta (e.g., change) between the patient's target BP and current BP and adjusts the "High" and "Low" BP alarm limits to alert the user if the BP drops, for instance, by 10% immediately and/or does not rise 30% higher in 20 minutes.

In another embodiment, heart rate (HR) parameter alert limits are modified based on administration of a chronotropic drug based on expected time therapeutic behaviors of the medication.

In another embodiment, respiratory rate alerts are modified with administration of sedative or opioid analgesics with known respiratory depressive action.

In another embodiment, a drug known to decrease or increase glomerular filtration rate (GFR) is administered, and fluid balance (I/O) alerts are set to an expected level. If the I/O balance is not achieved by that time, the clinician is alerted.

In another embodiment, via device interfacing, system interfacing, and/or user activation, system knowledge of the administration of a medication where the known side effects of the drug and dose are classified or "renal toxic" is employed. If, for instance, urine output has dropped, creatinine clearance has increased, or blood urea nitrogen (BU has increased (as indicated by laboratory results) in a certain time period to a certain limit, the user will receive an alert.

Figure 6:
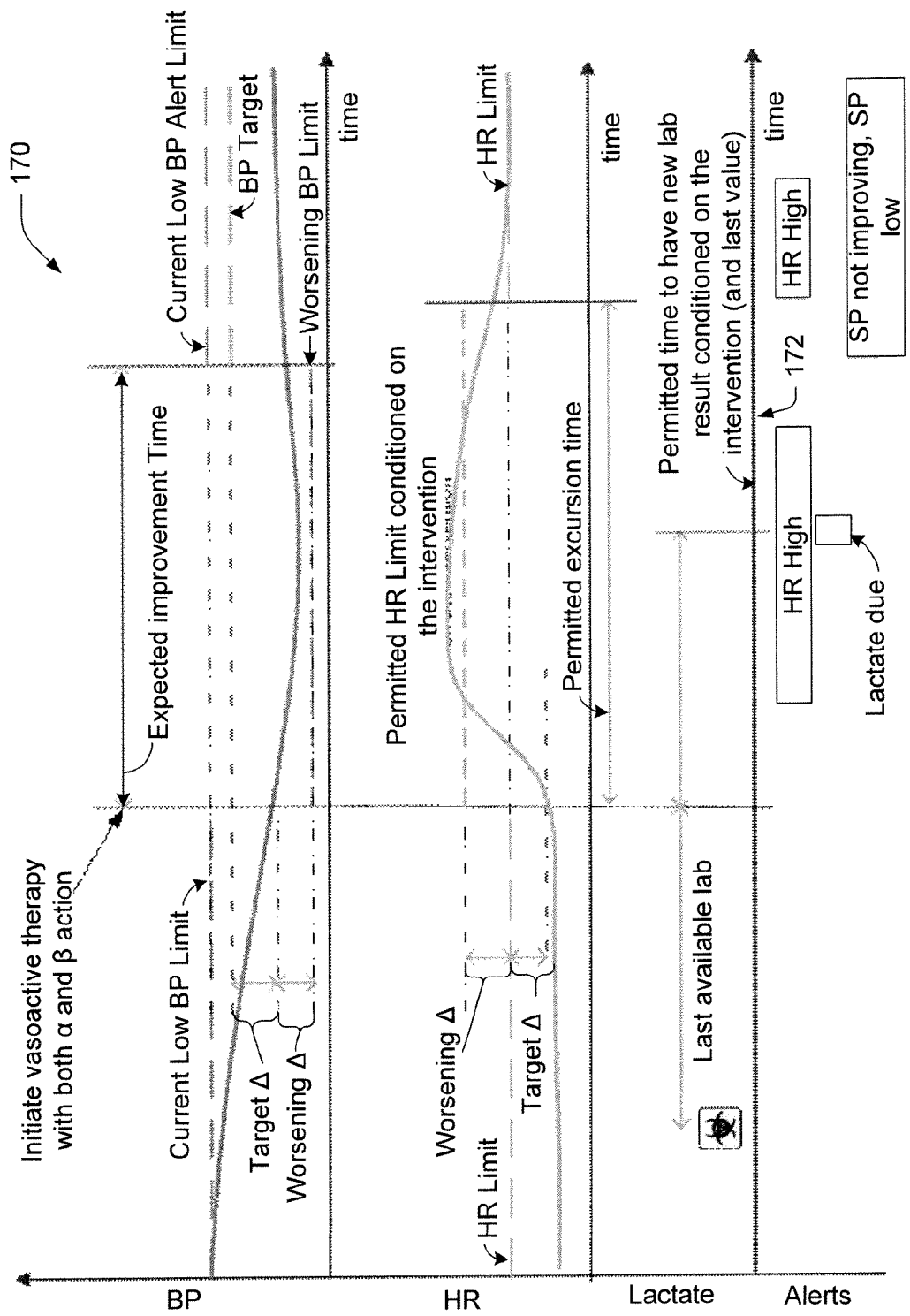
FIG. 6 illustrates a graph showing multiple physiologic parameters and clinical laboratory results create relevant parameter and workflow alerts.

FIG. 6 illustrates a graphic display 170 showing multiple monitored parameters, with multiple alert settings. According to an example, an intervention has a primary intended effect (e.g., to increase blood pressure (BP)) and two secondary unintended effects (e.g., increase heart rate (HR), increase lactate). The target BP \A (change) is based on either an absolute value or a percent improvement from the value at the intervention time. The worsening BP Δ (change) is based on a fixed percent below the BP value at the intervention time. The BP target is equal to the patient's BP at intervention time plus the target BP Δ (change). The expected improvement time is based on the intervention type. The worsening HR Δ is based on a fixed percent away from the current HR limit or value at the intervention time. The upper HR limit, in this example, is increased a fixed percent. Permitted excursion time is based on the intervention type and current value (or recent history). In this case, after the permitted excursion time expires, the previous HR limits are reinstated. Also represented in this example, the intervention is known to be associated with increase lactate production, so based on the last known lactate value, a permitted time 172 until new lab data is available is created. This time is based on the intervention type, how far away from the intervention the last lab was drawn, and the value of the last lab (normal, out of normal, critical value). Based on this example of physiologic events, the resulting alerts (e.g., high HR, Lactate due, BP low/not improving, etc.) are shown below the last time axis. For instance, and HR alarm is sounded when the HR limit is over the worsening A during the permitted excursion time period, and at the end of the permitted excursion time period if the HR is still above HR limit. In this example, each parameter is allowed to have independent threshold calculations, improvement times and recovery time functions.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A method of providing a time-varying physiological parameter alert, comprising:
    monitoring, via one or more sensors, a physiologic parameter, patient data, or clinical information of a patient; and
    via a processor programmed to perform the following:
        comparing the monitored physiologic parameter, patient data, or clinical information to an initial threshold criteria;
        following a drug administration, intervention or therapy administration event, temporarily changing the initial threshold criteria to a worsened condition threshold criteria that permits worsening of the monitored parameter for a duration of an allotted time period and to a post-administration threshold criteria after the allotted time period;
        determining whether the drug or therapy administration event is known to impact the monitored parameter by evaluating historical information about patient physiology lab study and alarm history;
        during the allotted time period, comparing the monitored parameter to the worsened condition threshold criteria when the drug or therapy administration event is known to impact the monitored parameter;
        after the allotted time period, comparing the monitored parameter to the post-administration threshold criteria; and
        in response to the monitored parameter violating one or more of the initial threshold criteria, the worsened condition threshold criteria, and the post-administration threshold criteria, triggering an alarm.

2. The method according to claim 1, wherein the worsened condition threshold criteria is constant.

3. The method according to claim 1, wherein the worsened condition threshold criteria diminishes to the post-administration target level in a plurality of steps.

4. The method according to claim 1, wherein the worsened condition threshold criteria is varied with time.

5. The method according to claim 1, wherein the worsened condition threshold criteria follows a monotonically decreasing or increasing curve, or an exponentially increasing or decreasing time function.

6. The method according to claim 1, further including:
    triggering an alert when the monitored parameter is not improved at the expiration of the allotted time period.

7. The method according to claim 1, further including determining whether the drug or therapy administration event is known to impact the monitored parameter by evaluating at least one of:
    available physiological patient information; and
    knowledge of administration or an intervention event that affects patient physiology.

8. The method according to claim 1, the monitored parameter including at least one of:
    ST segment elevation or depression;
    blood pressure;
    heart rate;
    blood-oxygen level;
    respiratory rate; and
    blood-metabolite level.

9. A non-transitory computer-readable medium carrying software for controlling the processor to configure and perform the method of claim 1.

10. The method according claim 1, wherein a notification of the drug administration, intervention or therapy administration event is manually input by a user.

11. The method according claim 1, where a notification of the drug administration, intervention or therapy administration event is automated.

12. A system that provides a time-varying physiological parameter alert to a user; comprising:
    one or more sensors that monitor a physiological parameter of a patient;
    a processor programmed to:
    receive one or more of patient data, clinical lab data, and monitored data or measurements that describe the physiological parameter;
    compare the monitored parameter to an initial threshold criteria;
    following a drug administration, intervention or therapy administration event, temporarily change the initial threshold criteria to a worsened condition threshold criteria that permits worsening of the monitored parameter for a duration of an allotted time period and to a post-administration threshold criteria after the allotted time period;
    determine whether the drug or therapy administration event is known to impact the monitored parameter by evaluating historical information about patient physiology lab study and alarm history;
    during the allotted time period, compare the monitored parameter to the worsened condition threshold criteria when the drug or therapy administration event is known to impact the monitored parameter;
    after the allotted time period, compare the monitored parameter to the post-administration threshold criteria; and
    in response to the monitored parameter violating one or more of the initial threshold criteria, the worsened condition threshold criteria, and the post-administration threshold criteria, trigger an alarm.

13. The system according to claim 12, wherein the worsened condition threshold criteria is constant.

14. The system according to claim 12, wherein the worsened condition threshold criteria diminishes or increases to the post-administration target level in a plurality of steps.

15. The system according to claim 12, wherein the worsened condition threshold criteria is varied with time.

16. The system according to claim 12, wherein the worsened condition threshold criteria follows a continuous curve, or an exponentially increasing or decreasing time function.

17. The system according to claim 12, wherein the processor triggers an alert when the monitored parameter is not improved at the expiration of the allotted time period.

18. The system according to claim 12, wherein the processor determines whether the drug or therapy administration event is known to impact the monitored parameter by evaluating at least one of:
    available physiological patient information; and
    knowledge of medicinal administration or an intervention event that affects patient physiology.

19. The system according to claim 12, the monitored parameter including at least one of:

ST segment elevation or depression;
blood pressure;
heart rate;
blood-oxygen level;
respiratory rate; and
blood-metabolite level.

20. The system according to claim 12, further including a user interface including:
- a display on which monitored parameter information is presented to the user along with threshold limit information; and
- an input device by which the user sets at least one threshold limit.

21. The system according claim 12, wherein a notification of the drug administration, intervention or therapy administration event is manually input by a user.

22. The system according claim 12, wherein a notification of the drug administration, intervention or therapy administration event is automated.

* * * * *